(12) United States Patent
Bergman et al.

(10) Patent No.: US 9,373,269 B2
(45) Date of Patent: Jun. 21, 2016

(54) PATCH PUMP TRAINING DEVICE

(71) Applicant: LifeScan Scotland Limited, Inverness-shire (GB)

(72) Inventors: Eric David Bergman, Menlo Park, CA (US); David Elder, Inverness (GB)

(73) Assignee: LifeScan Scotland Limited, Inverness (GB)

( * ) Notice: Subject to any disclaimer, the term of this patent is extended or adjusted under 35 U.S.C. 154(b) by 462 days.

(21) Appl. No.: 13/846,480

(22) Filed: Mar. 18, 2013

(65) Prior Publication Data

US 2014/0272861 A1 Sep. 18, 2014

(51) Int. Cl.
*G09B 23/28* (2006.01)
*A61M 5/142* (2006.01)
*G06F 19/00* (2011.01)

(52) U.S. Cl.
CPC ........... *G09B 23/28* (2013.01); *A61M 5/14248* (2013.01); *G06F 19/3406* (2013.01); *G09B 23/285* (2013.01); *A61M 2205/13* (2013.01); *A61M 2205/3317* (2013.01); *A61M 2205/3553* (2013.01); *A61M 2205/3561* (2013.01); *A61M 2205/3584* (2013.01); *A61M 2205/3592* (2013.01); *A61M 2205/43* (2013.01); *A61M 2205/44* (2013.01); *A61M 2205/50* (2013.01); *A61M 2205/502* (2013.01); *A61M 2205/52* (2013.01); *A61M 2205/581* (2013.01); *A61M 2205/582* (2013.01); *A61M 2205/583* (2013.01); *A61M 2205/8206* (2013.01); *A61M 2205/8287* (2013.01); *A61M 2210/04* (2013.01); *A61M 2230/65* (2013.01); *G06F 19/3468* (2013.01)

(58) Field of Classification Search
CPC .. A61M 5/14248; A61M 5/003; G09B 23/28; G09B 19/00
See application file for complete search history.

(56) References Cited

U.S. PATENT DOCUMENTS

| | | | |
|---|---|---|---|
| 5,860,957 A * | 1/1999 | Jacobsen et al. | 604/156 |
| 7,713,258 B2 | 5/2010 | Adams et al. | |
| 7,771,391 B2 | 8/2010 | Carter | |
| 7,927,306 B2 | 4/2011 | Cross et al. | |
| 7,931,621 B2 | 4/2011 | Cross et al. | |
| 7,976,493 B2 | 7/2011 | Carter et al. | |
| 7,976,500 B2 | 7/2011 | Adams et al. | |
| 8,062,256 B2 | 11/2011 | Carter et al. | |
| 8,128,596 B2 | 3/2012 | Carter | |
| 8,128,597 B2 | 3/2012 | Cross et al. | |
| 2002/0001794 A1* | 1/2002 | Melker et al. | 434/350 |
| 2002/0002326 A1* | 1/2002 | Causey et al. | 600/300 |
| 2003/0167035 A1* | 9/2003 | Flaherty et al. | 604/67 |
| 2004/0152065 A1 | 8/2004 | Witkowski | |

(Continued)

FOREIGN PATENT DOCUMENTS

WO 2006067217 A2 6/2006
WO 2012153295 A2 11/2012

OTHER PUBLICATIONS

International Search Report and Written Opinion issued in related International Patent Application No. PCT/EP2014/055305, mailed Jun. 12, 2014, 12 pages.

*Primary Examiner* — Robert J Utama

(57) ABSTRACT

Described are methods and systems to train a user in the proper operation of a manual patch pump to ensure that the user can attach the patch pump to a suitable location on the skin of the user and actuate the pump correctly in accordance with a prescribed dosing schedule or a self-calculated dosing schedule.

8 Claims, 3 Drawing Sheets

(56) References Cited

U.S. PATENT DOCUMENTS

| | | | |
|---|---|---|---|
| 2005/0022274 A1* | 1/2005 | Campbell et al. | D24/100 |
| 2007/0191702 A1* | 8/2007 | Yodfat et al. | 600/365 |
| 2007/0282269 A1 | 12/2007 | Carter et al. | |
| 2008/0071580 A1* | 3/2008 | Marcus et al. | 705/3 |
| 2008/0160492 A1* | 7/2008 | Campbell | G09B 19/00 434/379 |
| 2008/0269673 A1* | 10/2008 | Butoi et al. | 604/67 |
| 2008/0312512 A1* | 12/2008 | Brukalo et al. | 600/300 |
| 2009/0030366 A1* | 1/2009 | Hochman | 604/67 |
| 2009/0088690 A1 | 4/2009 | Carter et al. | |
| 2009/0088694 A1 | 4/2009 | Carter et al. | |
| 2009/0156989 A1 | 6/2009 | Carter et al. | |
| 2009/0326455 A1 | 12/2009 | Carter | |
| 2010/0114026 A1 | 5/2010 | Karratt et al. | |
| 2010/0179428 A1* | 7/2010 | Pedersen et al. | 600/443 |
| 2010/0332445 A1 | 12/2010 | Ray et al. | |
| 2011/0022025 A1* | 1/2011 | Savoie et al. | 604/500 |
| 2011/0098638 A1* | 4/2011 | Chawla et al. | 604/66 |
| 2011/0112484 A1 | 5/2011 | Carter et al. | |
| 2011/0124996 A1* | 5/2011 | Reinke et al. | 600/365 |

* cited by examiner

PATCH PUMP TRAINING DEVICE

BACKGROUND

Diabetes mellitus is a chronic metabolic disorder caused by an inability of the pancreas to produce sufficient amounts of the hormone drug so that the metabolism is unable to provide for the proper absorption of sugar and starch. This failure leads to hyperglycemia, i.e. the presence of an excessive amount of analyte within the blood plasma. Persistent hyperglycemia has been associated with a variety of serious symptoms and life threatening long term complications such as dehydration, ketoacidosis, diabetic coma, cardiovascular diseases, chronic renal failure, retinal damage and nerve damages with the risk of amputation of extremities. Because healing is not yet possible, a permanent therapy is necessary which provides constant glycemic control in order to always maintain the level of blood analyte within normal limits. Such glycemic control is achieved by regularly supplying external drug to the body of the patient to thereby reduce the elevated levels of blood analyte.

External drug was commonly administered by means of multiple, daily injections of a mixture of rapid and intermediate acting drug via a hypodermic syringe. While this treatment does not require the frequent estimation of blood analyte, it has been found that the degree of glycemic control achievable in this way is suboptimal because the delivery is unlike physiological drug production, according to which drug enters the bloodstream at a lower rate and over a more extended period of time. Improved glycemic control may be achieved by the so-called intensive drug therapy which is based on multiple daily injections, including one or two injections per day of long acting drug for providing basal drug and additional injections of rapidly acting drug before each meal in an amount proportional to the size of the meal. Although traditional syringes have at least partly been replaced by drug pens, the frequent injections are nevertheless very inconvenient for the patient, particularly those who are incapable of reliably self-administering injections.

Substantial improvements in diabetes therapy have been achieved by the development of the drug delivery device, relieving the patient of the need for syringes or drug pens and the administration of multiple, daily injections. The drug delivery device allows for the delivery of drug in a manner that bears greater similarity to the naturally occurring physiological processes and can be controlled to follow standard or individually modified protocols to give the patient better glycemic control.

In addition delivery directly into the intraperitoneal space or intravenously can be achieved by drug delivery devices. Drug delivery devices can be constructed as an implantable device for subcutaneous arrangement or can be constructed as an external device with an infusion set for subcutaneous infusion to the patient via the transcutaneous insertion of a catheter, cannula or a transdermal drug transport such as through a patch. External drug delivery devices are mounted on clothing, hidden beneath or inside clothing, or mounted on the body and are generally controlled via a user interface built-in to the device or on a separate remote device.

In recent years, parties have devised systems and devices for training operators on medical devices. For example, US Patent Application Publication No. 2002/0001794 to Melker et al., shows and describes a generic medical device training system which utilizes a series of sequential lessons for proper operation of the devices. US Patent Application No. 2004/0152065 to Witkowski shows a simulated device to educate users on the operation of a blood test meter and test strip.

These exemplary systems have shortcomings in that neither of Melker nor Witkowski allow for training in actual field conditions. The training is done in what is believed to be in unrealistic conditions using a generic handheld palm type computer (i.e., Melker) or a demonstration type model (i.e., Witkowski). Moreover, the training on Melker and Witkowski are predetermined such that the training cannot be customized for the user's particular health conditions.

SUMMARY OF THE DISCLOSURE

Applicants have devised techniques and methods to overcome the shortcomings identified in the art.

In one aspect, a patch type drug delivery pump training system is provided. The system includes a trainer device and a monitor device. The trainer device includes a base configured to be attached to a user's epidermis; a housing attached to the base, the housing having dosing actuator; a processor coupled to a memory, clock and dosing switches connected to the dosing actuators, the dosing switches configured to indicate dosing events whenever the dosing actuators have been actuated and such dosing events stored in the memory. The monitor device is disposed apart from the trainer device, the monitor device being configured to receive data from the memory of the trainer device. The data includes dosing events and time of each event so that the monitor device provides an indication of whether the user has actuated the dosing switches in accordance with a dosing plan stored in one of the monitor device or the trainer device.

In another aspect, a method of training a user on the use of an actual patch type drug delivery pump is provided. The actual patch pump is configured to deliver a drug stored in the pump body. The method can be achieved by: providing a dosing schedule of the drug to the user; providing a trainer device to the user, the device having a dummy or simulated housing and dummy or simulated actuators similar in shape and size as the actual patch type drug delivery pump, the dummy or simulated housing containing a processor and memory coupled to respective switches of the dummy or simulated actuators; furnishing the user with a dosing schedule; actuating the dummy or simulated actuators; recording activation of the switches for the dummy or simulated actuators and the time at which such activation occurred into the memory to provide a record of training dosage events; and outputting the record to provide for a comparison between training usages of the trainer device as compared to the dosing schedule.

In yet a further method, a method of training a user on the use of an actual patch type drug delivery pump is provided. The actual patch pump is configured to deliver a drug stored in the pump body. The method can be achieved by providing a dosing schedule of the drug to the user; providing a trainer device to the user, the device having a dummy or simulated housing and dummy or simulated actuators similar in shape and size as the actual patch type drug delivery pump, the dummy or simulated housing containing a processor and memory coupled to respective switches of the dummy or simulated actuators; annunciating to the user the dosing schedule; recording activation of the switches for the dummy or simulated actuators and the time at which such activation occurred into the memory to provide a record of training dosage events; and outputting the record to provide for a comparison between training usages of the trainer device as compared to the dosing schedule.

And for these aspects, the following features may also be utilized in various combinations with these previously disclosed aspects: the monitor device may include a smartphone programmed to receive data transmitted by the trainer device by a suitable wireless protocol; the wireless protocol is selected from one of a Bluetooth, WiFi, RFID, or a Near-Field-communication protocol; the trainer device further may include a power source connected to the processor of the trainer device; the trainer further may include: an audio output connected to the processor to provide the indication in audible form; a visual output connected to the processor to provide the indication in visual form; and a wireless transmitter connected to the processor to transmit the data to the monitor device; the base further may include at least one sensor configured to determine a suitable location for a drug delivery pump based on the impedance of the epidermis at which the housing is attached thereto; the sensor may include at least two electrodes configured to contact the epidermis and transmit an alternating signal between the at least two electrodes; the sensor may include at least two electrodes configured to measure capacitance of the epidermis at a location of attachment of the trainer device; the method may further include comparing a time at which actuating of the dummy actuators is taking place and the time prescribed by the dosing schedule; in the event at which the time prescribed in the dosing schedule is not within a predetermined time period of the actuating step, recording noncompliance of the dosing schedule in the memory; or in the event at which the prescribed time for dosing is within a predetermined time period of the actuating step, recording a compliance with the dosing schedule in the memory. Alternatively, the recording of an error may include annunciating a negative feedback to the user at the time the recording is made; the recording of the compliance may include annunciating of a positive feedback to the user at the time the recording is made; the outputting may include displaying a graphical representation of time at which one or more actuations have occurred and the prescribed dose at the prescribed time; the predetermined time period may include any time period from about 10 minutes to about 60 minutes.

In the aforementioned aspects of the disclosure, the steps of the described method may be performed by an electronic circuit or a processor. These steps may also be implemented as executable instructions stored on a computer readable medium; the instructions, when executed by a computer may perform the steps of any one of the aforementioned methods.

In additional aspects of the disclosure, there are computer readable media, each medium comprising executable instructions, which, when executed by a computer, perform the steps of any one of the aforementioned methods.

In additional aspects of the disclosure, there are devices, such as test meters or analyte testing devices, each device or meter comprising an electronic circuit or processor configured to perform the steps of any one of the aforementioned methods.

These and other embodiments, features and advantages will become apparent to those skilled in the art when taken with reference to the following more detailed description of various exemplary embodiments of the invention in conjunction with the accompanying drawings that are first briefly described.

BRIEF DESCRIPTION OF THE DRAWINGS

The accompanying drawings, which are incorporated herein and constitute part of this specification, illustrate presently preferred embodiments of the invention, and, together with the general description given above and the detailed description given below, serve to explain features of the invention (wherein like numerals represent like elements).

MODES FOR CARRYING OUT THE INVENTION

The following detailed description should be read with reference to the drawings, in which like elements in different drawings are identically numbered. The drawings, which are not necessarily to scale, depict selected embodiments and are not intended to limit the scope of the invention. The detailed description illustrates by way of example, not by way of limitation, the principles of the invention. This description will clearly enable one skilled in the art to make and use the invention, and describes several embodiments, adaptations, variations, alternatives and uses of the invention, including what is presently believed to be the best mode of carrying out the invention.

As used herein, the terms "about" or "approximately" for any numerical values or ranges indicate a suitable dimensional tolerance that allows the part or collection of components to function for its intended purpose as described herein. In addition, as used herein, the terms "patient," "host," "user," and "subject" refer to any human or animal subject and are not intended to limit the systems or methods to human use, although use of the subject invention in a human patient represents a preferred embodiment. Furthermore, the term "user" includes not only the patient using a drug infusion device but also the caretakers (e.g., parent or guardian, nursing staff or home care employee). The term "drug" may include pharmaceuticals or other chemicals that causes a biological response in the body of a user or patient. The term "annunciate" and variations on its root term indicate that an announcement may be provided via text, audio, visual or a combination of all modes or mediums of communication to a user.

Figure 1:
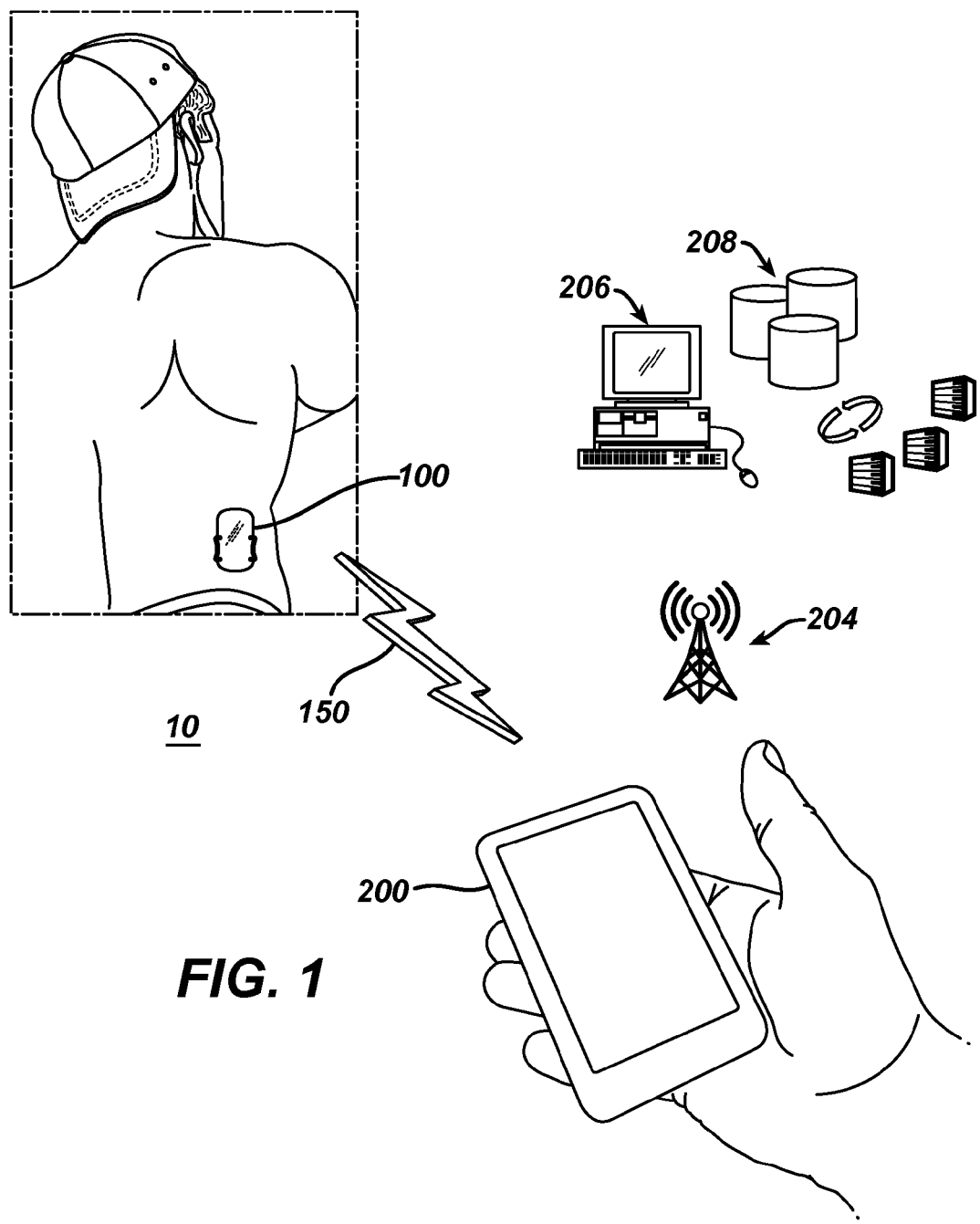
FIG. 1 illustrates an exemplary embodiment of the training system for a patch pump.

FIG. 1 illustrates a patch pump training system 10 according to an exemplary embodiment. Patch pump training system 10 includes a patch pump trainer 100 and a remote monitor 200. Patch pump trainer 100 is configured to transmit and receive data to and from remote monitor 200 by, for example, radio frequency communication 150. Patch pump trainer 100 may also function as a stand-alone device with its own built in controller. In one embodiment, patch pump trainer 100 is a simulated patch pump device and remote monitor 200 is a hand-held portable monitor such as, for example, a smartphone, mobile phone or a bespoke monitor and wireless communication transceiver using any suitable communication protocol such as for example, BlueTooth Low Power, WiFi, RFID, NFC and equivalents thereof. In such an embodiment, data transmitted from patch pump trainer 100 to a remote network directly or via a remote monitor 200 may include information such as, for example, dosing events, time of dosing events and dosage delivered or undelivered, the state of internal battery charge, or any internal system errors. Alternatively, housing temperature, or any sharp acceleration indicating device abuse (hard knocks) can be sensed by a sensor or a combination of sensors mounted or built into the device. Also device attachment information from the capacitive sensors are provided to indicate if the device was initially attached properly, or if it has come loose in operation, to name a few. Data transmitted from remote monitor 200 to patch pump trainer 100 may include a dosing schedule, time and date, software update, messages to the trainee or user regarding changes in dosing schedule, carb information of simulated meal intake and the like. Alternatively, the remote monitor 200 may perform other functionalities with the trainer device 100 such as for example, providing messages or instructions to the user to perform other tasks such as checking for proper mounting of the pump.

Each of the devices 100 and 200 has a suitable microcontroller (not shown for brevity) programmed to carry out various functionalities. For example, a microcontroller can be in the form of a mixed signal microprocessor (MSP) for each of the devices 100 or 200. Such MSP may be, for example, the Texas Instrument MSP Model430, as described in patent application publication numbers US2010-0332445, and US2008-0312512 which are incorporated by reference in their entirety herein. The MSP Model430 or the pre-existing microprocessor of each of these devices can be configured to also perform the method described and illustrated herein.

Patch pump trainer 100 may also be configured for bi-directional wireless communication with a remote health monitoring station 206 through, for example, a wireless communication network 204. Remote monitor 200 and remote monitoring station 206 may also be configured for bi-directional wired communication through, for example, a telephone land based communication network. Remote monitoring station 206 may be used, for example, to download upgraded software to patch pump trainer 100 and to process information from patch pump trainer 100. Examples of remote monitoring station 206 may include, but are not limited to, a personal or networked computer, a personal digital assistant, SmartPhones, other mobile telephone, a hospital base monitoring station or a dedicated remote clinical monitoring station.

Figure 2:
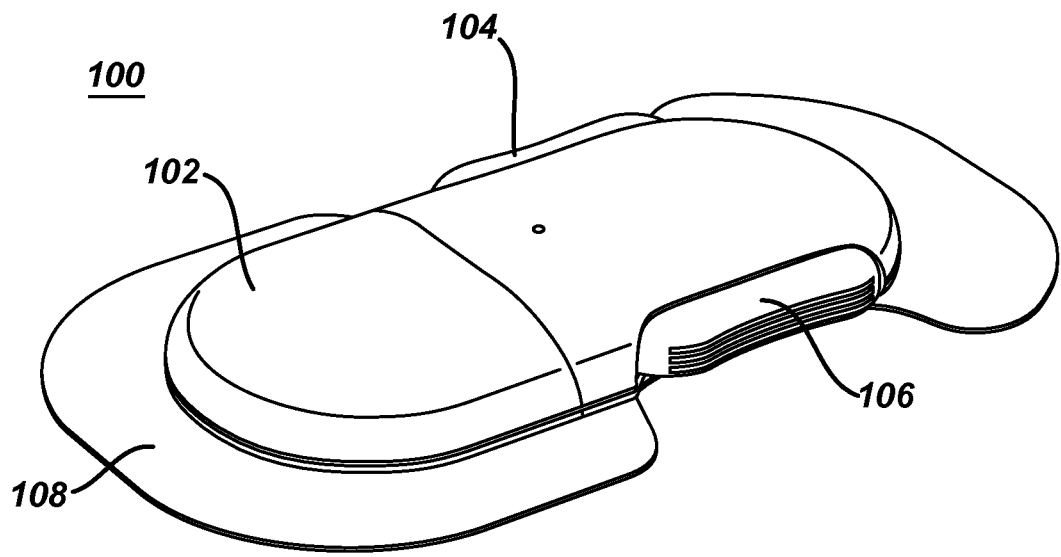
FIG. 2 illustrates the training device of FIG. 1.

FIG. 2 illustrates the training patch pump device 100 in a perspective view. The trainer device 100 includes a dummy or simulated housing 102 with first dummy or simulated actuator bar 104 and second dummy or simulated actuator bar 106. The housing 102 is mounted to a base 108 which can be in the form of a flexible member with adhesive disposed on the underside of the member for attachment to the epidermis of a user. As used herein, the term "dummy" or "simulated" is used to indicate that the subject component referenced as "dummy" does not have the same function as in the actual patch pump device, which is shown and described in U.S. Pat. Nos. 7,976,500; 7,771,391; 7,976,493; 8,128,597; 7,927,306; 8,062,256; 8,128,596 and in US Patent Application Publication Nos. 2009/0088694; 2009/0156989; 2009/0326455; 2009/088690; 2011/0112484, all of these noted disclosures are hereby incorporated by reference into this application as if fully set forth herein.

Figure 3:
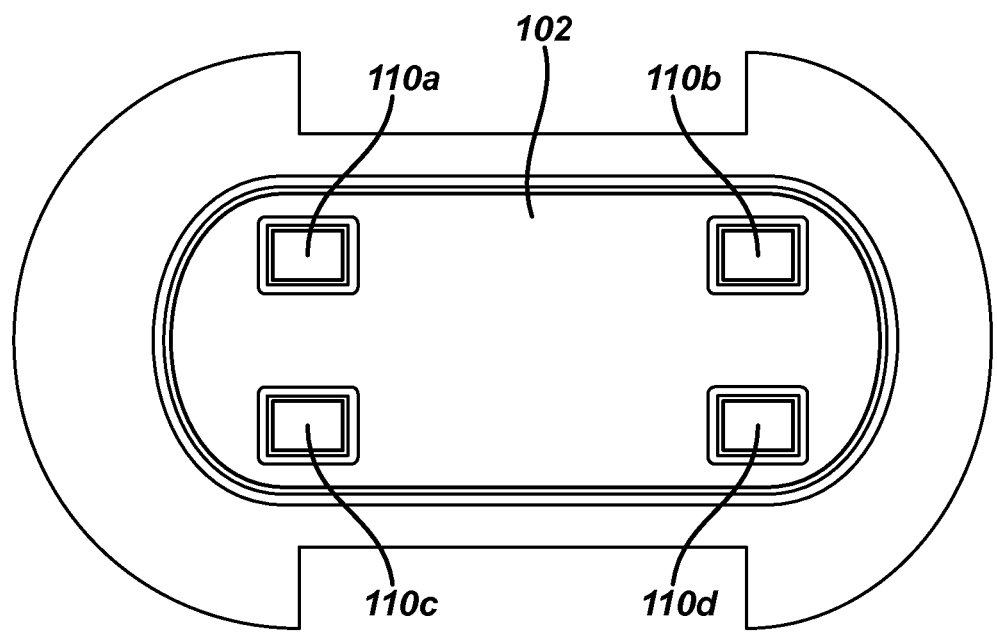
FIG. 3 illustrates a plan view of the underside of the training device in FIG. 2 to show the sensors for the adhesive patch.

FIG. 3 illustrates a plan view of the underside of housing 102 with base member 108. The based member 108 can be provided with a suitable adhesive for attachment to the skin of the user. The underside of housing 102 can be provided with at least one resistance or impedance sensor(s). In the preferred embodiments, there are four sensors 110a, 110b, 110c, and 110d provided to allow the sensors to determine if the location for placement of the dummy patch pump 100 is at the appropriate location with sufficient interstitial tissues for delivery of drugs had the device 100 been an actual drug delivery device. Each of the sensors can include at least one electrode to allow the electrode to drive at least one alternating signal into the epidermis for sensing of the differential signal returning from the epidermis. Alternatively, one sensor (e.g., 110a) may drive at least one alternating signal into the epidermis so that a determination of whether the device was mounted to the skin by comparing the signals to see if the device is in firm contact with the skin. The electrode(s) of each sensor may be configured to pierce the skin but without extending into the dermis layer containing the blood vessels or the nerves and thereby would be virtually painless. Alternatively, the electrodes may not need to pierce the skin to detect surface capacitance. That is, the electrodes may not need to be in contact with the skin by utilizing the projected capacitance technique similar to touchscreen technology. The sensors can operate to measure impedance with signal frequencies from about 5 kHz to about 1 MHz. Where the impedance measured by the sensor is high as compared to a predetermined threshold, the processor would indicate to the user that the site for adhering could be inappropriate or that the patch pump is not fully attached to the epidermis. Alternatively, the sensors can be capacitive type sensors using DC signals. Where the capacitance measured by the sensors is low, the processor would indicate, as before, that the patch pump is not fully attached to the site due to the poor contact of the sensors with the skin.

Figure 4:
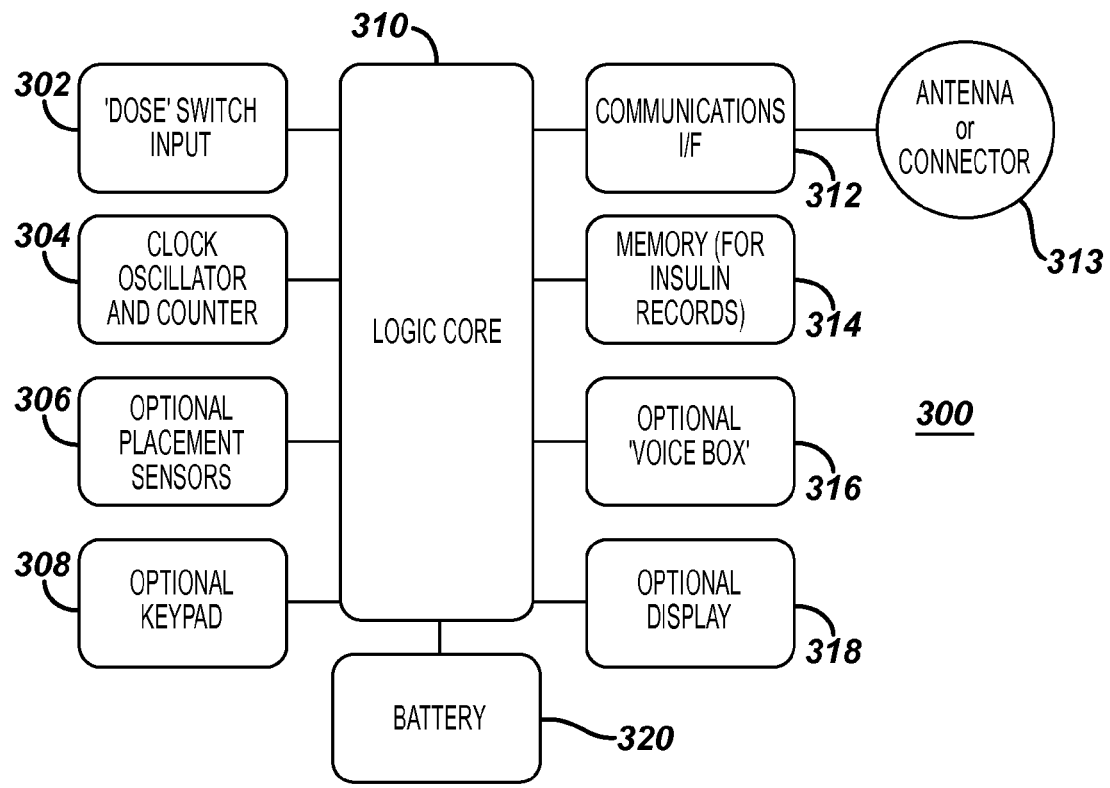
FIG. 4 illustrates a system architecture of the components disposed inside the training device of FIG. 1.

Although keys, keypads, speaker, piezo-electric transducer, and a low-cost low powered display are not shown in the Figures for brevity, such components are implemented with the device as provided in the system architecture shown in FIG. 4.

FIG. 4 illustrates the architecture of the trainer device 100. In trainer device 100, the electrical components may include a central processing unit 310 (e.g., microprocessor or microcontroller) and memory storage 314 for storing control programs and operation data. A radio frequency transceiver module 312 is provided for sending and receiving communication signals (i.e., messages, data, and information) to/from remote monitor 200. A display 318 can be provided for operational information to the user. A plurality of navigational keypad 308 (details not shown) for the user to input information. An alarm or voice box 316 (e.g., visual, auditory or tactile) can be connected to the processor 310 for immediate feedback to the user by annunciating negative or positive feedbacks. As used here, the term "annunciate" or "annunciating" and variations on the root term indicate that an announcement may be provided via text, audio, visual or a combination of all modes of communication. Alternatively, a simple vibrator can also be used in place of the voice box 316. Respective switches 302 can be coupled to the dummy actuator 106 so that upon actuation of dummy actuator 106, one or both of the switches 302 close a detection circuit, thereby indicating to the processing unit 310 that the user has conducted a dosing event for the purpose of training (even though there is no dosing taking place). Because the actual patch pump requires both dosing actuators to be actuated at about the same time for a proper dosing, the processor unit will recognize if only one of the two buttons has been actuated. In such case, the processor would detect that the user has improperly actuated the dosing buttons and store a record of such improper dosing. The switches 302 can be displacement sensitive such that the processing unit 310 will be able to recognize if the user has fully depressed each of the dummy actuator bars 104 and 106. In the event the user has not fully compressed one or both of the actuator bars 104 and 106 (which would be indicated by an audible click on the actual patch pump and necessary for the actual pump to deliver the correct dosage), the processing unit 310 will recognize this partial displacement of the actuator bars 104 and 106 as an improper actuation and record such event as an improper dosing event. A clock 304 is connected to the processing unit 310 so that the time at which a dosing event occur (and which event may be flagged or tagged as proper or improper).

It is noted that while the device 100 is shown with a battery power supply, the device 100 can be a Near-Field-Communication ("NFC") enabled device so that its functionalities can be powered by the NFC equipped monitor 200 (or an NFC enabled SmartPhone) with the NFC enabled monitor close by.

In operation, the user or the health-care-provider ("HCP") would attach the trainer device 100 onto an appropriate location on the outer skin layer of the user. The trainer device 100 can be attached directly if the patch pump has a user insertable needle and cannula. Alternatively, the device can be used with an inserter device such as that shown and described in U.S. Pat. Nos. 7,713,258; 7,931,621; or US Patent Application Publication No. 2007/0282269, which are hereby incorporated by reference as if fully set forth herein. Where the trainer device 100 includes sensors 110a-110d, the sensors could indicate to the user (or trainee) via the voicebox or display whether the device has been attached evenly across the epidermis. Next, the user is provided with a schedule or directions to begin actuation of the trainer device as if insulin would actually be given. Over the course of several days, the HCP would monitor the trainer device 100 remotely over the network 204 using a monitor 200 provided to the user. Alternatively, a software program can be loaded into a SmartPhone (e.g., iPhone or Android) for use with a Near-Field wireless built into both the trainer device 100 and the SmartPhone. Data collected from the trainer device 100 can be used by the monitor device 200 (or a SmartPhone) would be immediately communicated to the user via the monitor 200. Data collected over 12 or more hours could be used to show whether the user is in compliance with a dosing schedule configured into the monitor 200 (or SmartPhone) or the user's own calculation for boluses to be given over a period of time. The user's calculated boluses can be imported or entered into the memory of the device 100 or the monitor 200. The HCP's prescribed dosing schedule or the user's own calculated dosing schedule would then be used to determine if correct usage of the trainer device 100 has been followed.

In particular, applicants have devised a method to train users on operation of a patch pump. The method can be achieved by: providing a dosing schedule of the drug to the user. The dosing schedule can be one generated by the HCP or by the user using his or her own bolus calculation. Thereafter, a trainer device is provided to the user and the dosing schedule can be entered via monitor 200 or directly via Near-Field communication or any other short range communication RF such as BlueTooth; BTLE, WiFi, or a proprietary RF with the HCP's computer 206. The user, following the schedule, would actuate the dummy actuators. This would cause the processor to record the activation of the switches for the dummy actuators and the time at which such activation occurred into the memory to provide a record of training dosage events. The device 100 can output the record directly to the user via the voicebox or display or to the monitor 200. This would provide for a comparison between training usages of the trainer device as compared to the dosing schedule. In this comparison, the processor can be programmed to compare a time at which actuating of the dummy actuators is taking place and the time prescribed by the dosing schedule (which can be prescribed by the HCP or generated by the user's own calculation). In the event at which the time prescribed in the dosing schedule is not within a predetermined time period (e.g., from about 10 to about 30 minutes) of the actuating step, the processor can record the noncompliance of the dosing schedule in the memory. On the other hand, in the event at which the prescribed time for dosing is within the predetermined time (e.g., from about 10 to about 30 minutes) of the actuating step, the system would record a compliance with the dosing schedule in the memory.

Figure 5:
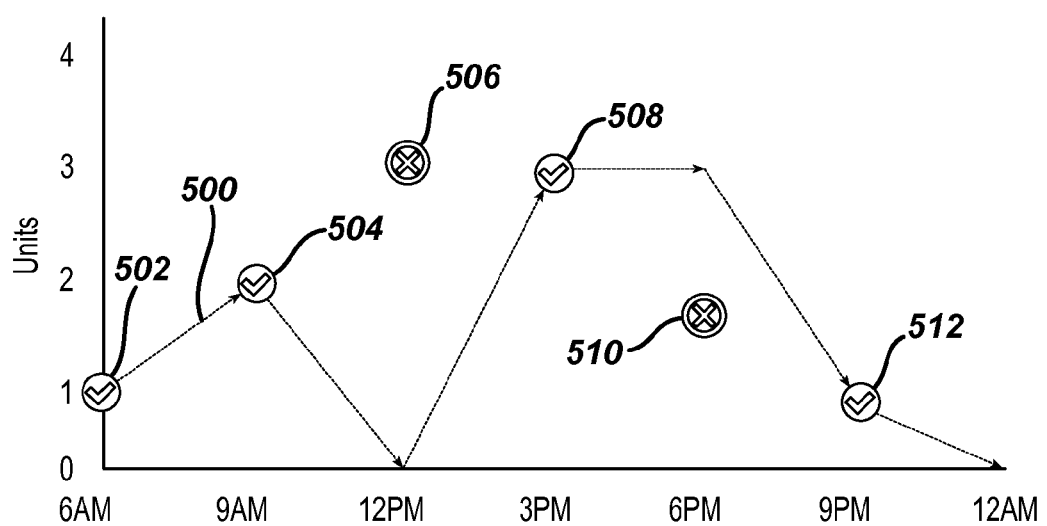
FIG. 5 illustrates an exemplary graphical report of the user's performance in real-life conditions.

In the operational example above, the monitor 200 could provide a graphical presentation in the display, shown here in FIG. 5, of when the user has been in compliance with the prescribed dosing schedule (in the form of a check mark or a suitable indicia or icon) or not in compliance (in the form of an X or a suitable indicia or icon).

As shown in FIG. 5, the user has been prescribed by the HCP or the trainer device 100 has been programmed with a schedule 500 for a period of 18 hours (e.g., during waking hours). In this schedule 500, a first unit of insulin (or one squeeze of the dummy actuator bars 104 and 106 on the trainer device 100) is to be given a 6 AM, with 2 units at 9 AM and zero units at noon. At 3 PM, 3 units (or three squeezes of the actuator bars 104 and 106) are to be given with 3 units again at 6 PM and 1 unit at 9 PM. A HCP, or even the user, reviewing the data displayed would immediately see that the user carried out an appropriate dosing at 502, 504, 508, and 512 (noted by check mark "✓") but gave an inappropriate dosages at 12 PM ("X" noted 506) and again at 6 PM (X noted at 510).

Instead of reviewing the user's dosing pattern, the device 100 or the monitor 200 could immediately provide feedback to the user with appropriate annunciation of negative feedback where the user has used the device incorrectly. On the other hand, the device 100 or monitor 200 can also provide positive feedback immediately after the user has operated the device 100 correctly. Both the negative and positive feedbacks provide "in the moment" training such that when the user is using the actual fully functioning patch pump, the user would use such pump correctly due to the prior training provided by device 100.

In yet another scenario, the trainer device 100 can itself provide test scenarios to the user. For example, the trainer device 100 (or monitor 200) can provide a series of voice prompts for doses to be administered by the user. In these sequences, a trainer device would be provided to the user. As before, the device has a dummy housing and dummy actuators similar in shape and size as the actual patch type drug delivery pump that contains a processor and memory coupled to respective switches of the dummy actuators. In use, the device would annunciate to the user a sequence of actuation steps within a predetermined time period dosing schedule. The user is expected to follow the annunciated instruction actuate the dummy actuators in the prescribed sequence. The processor would record the activation of the switches for the dummy actuators and the time at which such activation occurred into the memory to provide a record of training dosage events. Once the annunciated sequences have been completed (typically from 10 to 60 minutes), the device would output the record (directly to the user or the HCP) to provide for a comparison between training usages of the trainer device as compared to the dosing schedule.

The duration of such type of short test sequence can be from about 10 minutes to 60 minutes and preferably less than one hour and most preferably less than 30 minutes. At the end of the series of training prompts, the device can store the user's success versus failure score which can be reported immediately to the user or to the HCP via a direct transmission from device 100 directly to the HCP (or from device 100 to monitor 200 then from monitor 200 to the HCP) via network 204 to the HCP's computer 206 or mobile computer (e.g., laptop or SmartPhone). Alternatively, the test sequences can be conducted in the presence of the HCP or training operator to ensure that any questions or error can be addressed immediately.

While the invention has been described in terms of particular variations and illustrative figures, those of ordinary skill in the art will recognize that the invention is not limited to the variations or figures described. In addition, where methods and steps described above indicate certain events occurring in certain order, those of ordinary skill in the art will recognize that the ordering of certain steps may be modified and that such modifications are in accordance with the variations of the invention. Additionally, certain of the steps may be performed concurrently in a parallel process when possible, as well as performed sequentially as described above. Therefore, to the extent there are variations of the invention, which are within the spirit of the disclosure or equivalent to the inventions found in the claims, it is the intent that this patent will cover those variations as well.

What is claimed is:

1. A patch type drug delivery pump training system comprising:
    a trainer device including:
        a base configured to be attached to a user's epidermis;
        a housing attached to the base, the housing having at least one dosing actuator, a processor coupled to a memory, clock and dosing switches connected to the dosing actuators, the dosing switches configured to indicate dosing events whenever the dosing actuators have been actuated and such dosing events stored in the memory; and
    a monitor device disposed apart from the trainer device and operatively connected therewith, wherein the monitor device initiates at least one test scenario that simulates the delivery of a drug and receives data from the memory of the trainer device, the data including simulated dosing events and time of each event so that the monitor device provides an indication of whether the user has actuated the dosing switches in accordance with a dosing plan stored in one of the monitor device or the trainer device, wherein the monitor device provides training feedback to the user at the time of receiving the data from the trainer device, the training feedback indicating compliance or noncompliance with the at least one test scenario.

2. The system of claim 1, in which the monitor device comprises a smartphone programmed to receive data transmitted by the trainer device by a suitable wireless protocol.

3. The system of claim 2, in which the wireless protocol is selected from one of a Bluetooth, WiFi, RFID, or a Near-Field-communication protocol.

4. The system of claim 1, in which the trainer device further comprises a power source connected to the processor of the trainer device.

5. The system of claim 1, in which the trainer device further comprises:
    an audio output connected to the processor to provide the indication in audible form;
    a visual output connected to the processor to provide the indication in visual form; and
    a wireless transmitter connected to the processor to transmit the data to the monitor device.

6. The system of claim 1, in which the base further comprises at least one sensor configured to determine a suitable location for a drug delivery pump based on the impedance of the epidermis at which the housing is attached thereto.

7. The system of claim 6, in which the sensor comprises at least two electrodes configured to contact the epidermis and transmit an alternating signal between the at least two electrodes.

8. The system of claim 6, in which the sensor comprises at least two electrodes configured to measure capacitance of the epidermis at a location of attachment of the trainer device.

* * * * *